United States Patent [19]

Backer

[11] Patent Number: 4,706,668

[45] Date of Patent: Nov. 17, 1987

[54] ANEURYSM CLIP PLIERS

[75] Inventor: Robert Backer, Cincinnati, Ohio

[73] Assignee: B & B Tools, Cincinnati, Ohio

[21] Appl. No.: 776,229

[22] Filed: Sep. 16, 1985

[51] Int. Cl.4 ............................................. A61B 17/12
[52] U.S. Cl. .................................... 128/325; 128/346
[58] Field of Search ................................ 128/321–322, 128/325–326, 345, 346

[56] References Cited

U.S. PATENT DOCUMENTS

| Re. 27,146 | 6/1971 | Rozmus | 30/193 |
| 3,805,792 | 4/1974 | Cogley | 128/325 |
| 4,038,987 | 8/1977 | Komiya | 128/321 |
| 4,241,734 | 12/1980 | Kandel et al. | 128/325 |
| 4,246,903 | 1/1981 | Larkin | 128/325 |
| 4,367,746 | 1/1983 | Derechinsky | 128/325 |
| 4,562,839 | 1/1986 | Blake et al. | 128/326 |
| 4,602,631 | 7/1986 | Funatsu | 128/321 |

Primary Examiner—Dalton L. Truluck
Attorney, Agent, or Firm—Frost & Jacobs

[57] ABSTRACT

Disclosed is an aneurysm clip pliers for applying an aneurysm clip to a blood vessel. The pliers have a hand grip end and a barrel end. A pusher bar reciprocates within the hollow barrel portion causing the Y-shaped clip grip to open or close, depending upon the position of the push rod. A trigger mechanism causes the spring loaded pusher bar to shift toward the Y-shaped grip when the trigger is squeezed. A locking mechanism enables an aneurysm clip to be placed between the arms of the Y-shaped grip and retained therein until the aneurysm clip is to be applied on the blood vessel. The barrel end is rotatable through 360° with respect to the hand grip end of the aneurysm clip pliers, and the Y-shaped grip permits the aneurysm clip to pivot about an arc slightly larger than 180°. Accordingly, positioning the aneurysm clip on the defective blood vessel is easily accomplished.

7 Claims, 6 Drawing Figures

U.S. Patent  Nov. 17, 1987  Sheet 1 of 3  4,706,668
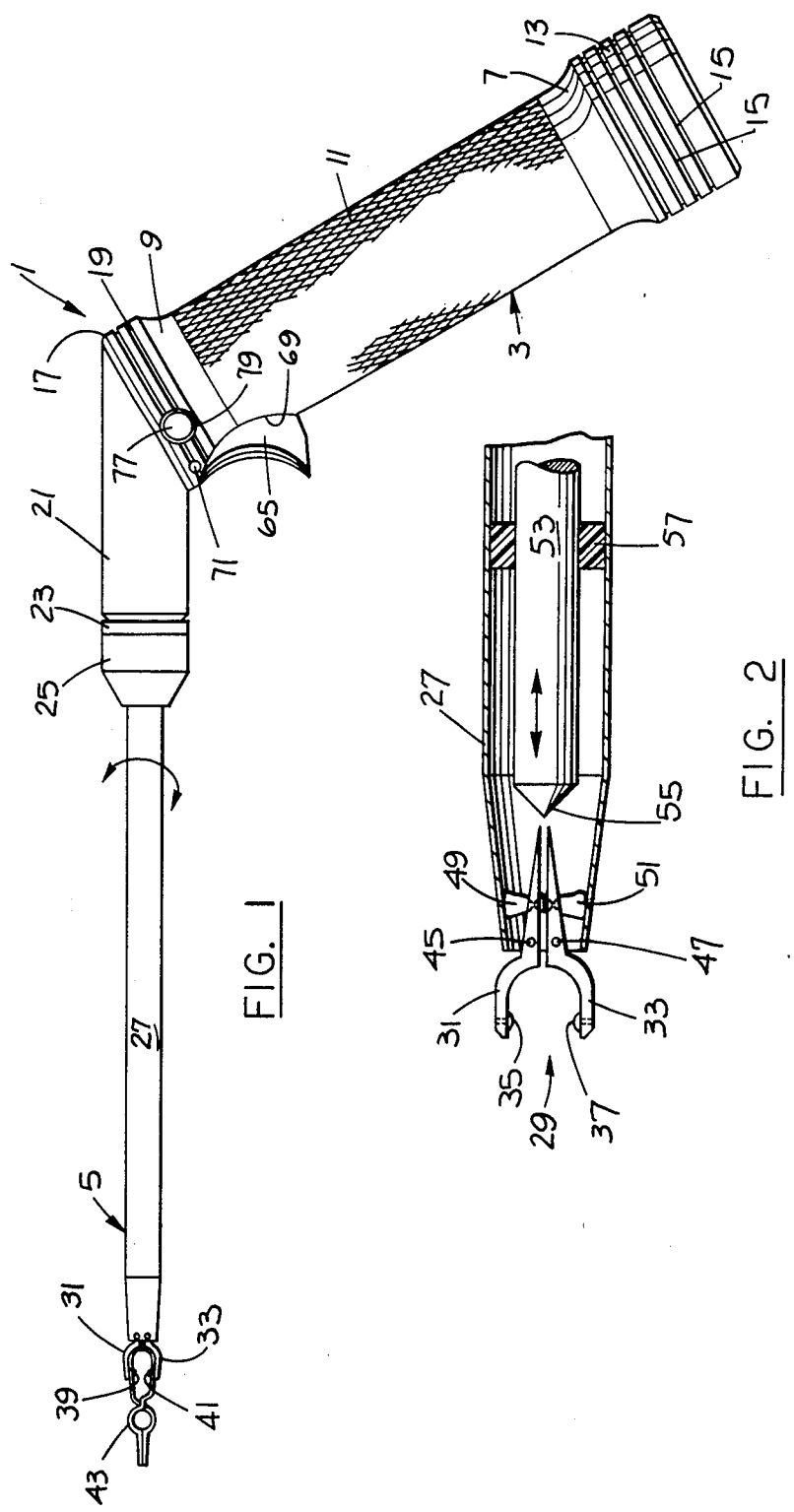

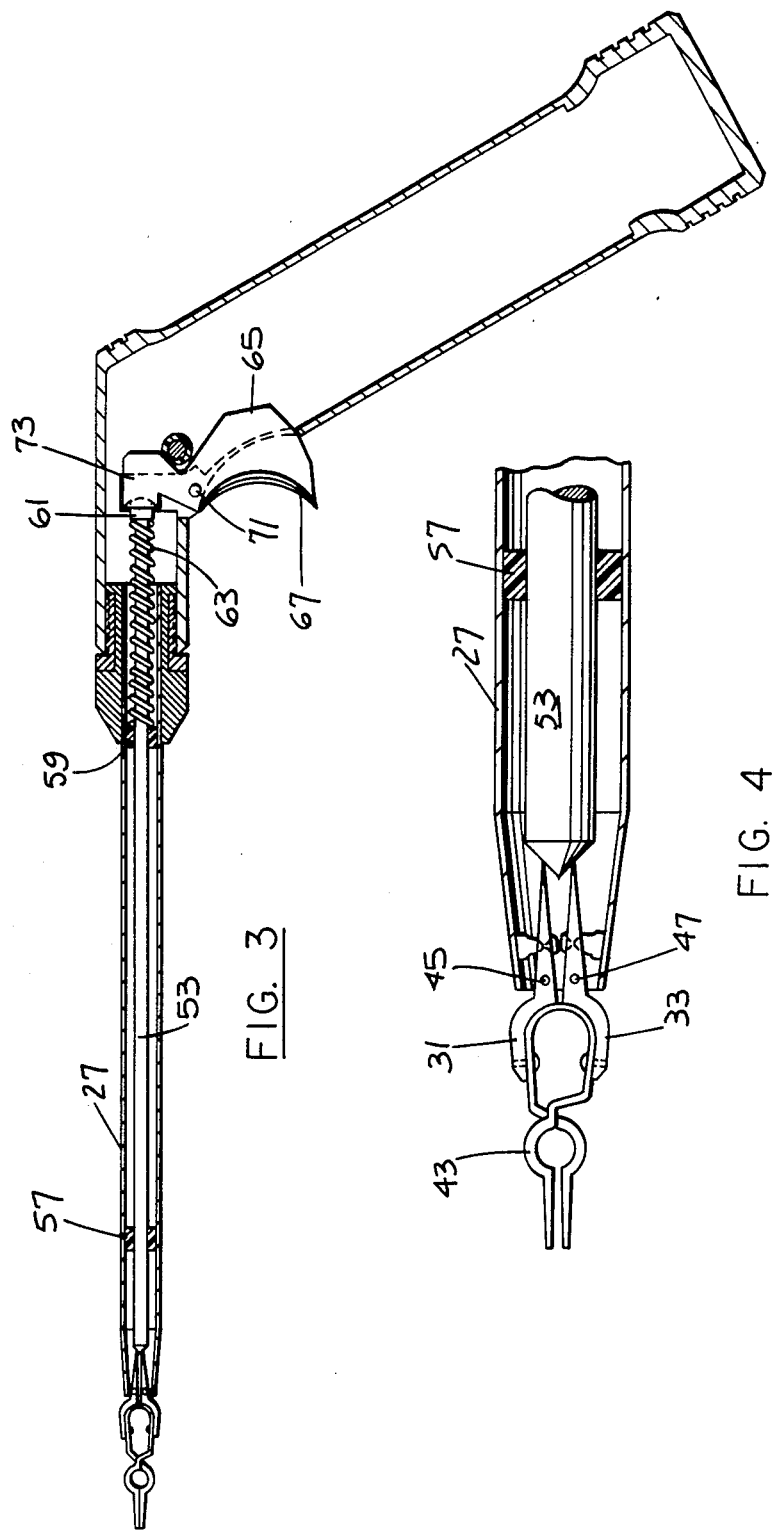

ANEURYSM CLIP PLIERS

BACKGROUND OF THE INVENTION

(1) Field of the Invention

The present invention pertains to a tool designed to hold an aneurysm clip and to be manually activated by a surgeon to apply the clip to a blood vessel in the brain. In particular, the present invention pertains to pliers adapted to hold and apply an aneurysm clip on a blood vessel wherein the pliers have a small dimension adjacent the aneurysm clip so as to be capable of projecting through a small opening in the skull of a patient.

(2) Prior Art

Conventional clip appliers for aneurysm clips are simplistic in design and limited in function with respect to their ability to apply an aneurysm clip. Generally, prior art clip appliers consisted of an elongated handle portion at the end opposite the clip retaining end. These clip appliers operated on a scissors-type principle so that when the elongated handle portion is squeezed together, the clip applier ends pivot about a rivet or axle and approach one another. When an aneurysm clip is positioned between the clip ends and the handle portion is squeezed together, the aneurysm clip opens so that it may be applied to a blood vessel by a surgeon. These scissor-type clip appliers have been in existence a long time and little to no progress has been made in their design. Moreover, because the design is very simplistic, it is limited in its application in that a surgeon must contort his hand, wrist and arm in order to apply the clip on a blood vessel in a difficult or remote location. Often, contortion of the surgeon's hand, wrist and arm cause the surgeon to lose manual dexterity resulting in the clip being applied incompletely or improperly. Furthermore, the contortion of the surgeon's hand, wrist and arm often block the surgeon's view of the blood vessel to which the clip is to be applied. In order to aid the physician in obtaining access to a remotely located blood vessel, conventional aneurysm clips often were available in which the contact portion of the clip is angled with respect to the remainder of the clip. However, these type of aneurysm clips could only alleviate the contortion of the surgeon's hand, wrist or arm in one direction.

Another common problem with conventional aneurysm clip appliers is that the tool is spring biased completely open. This requires the physician or surgeon to load the aneurysm clip within the applier, rather than having a tray with several clip appliers loaded with an aneurysm clip. If an applier were fully loaded and ready to use, a nurse could hand the applier to the surgeon when desired.

Conventional aneurysm clip appliers are illustrated in the Codman Surgical Instrument Catalog, pages 329-335. The following U.S. patent references further illustrate the aneurysm clip applier.

U.S. Pat. No. 2,876,778 to Kees, issued on Mar. 10, 1959, discloses a scissors-type aneurysm clip applier which is spring-biased open. Each free end of the applier is hooked so that a clip may be retained between the hooked ends. A plate enables a clip to be placed between the hooked ends and retained in such a position until the surgeon is ready to apply the clip to a blood vessel. Although this aneurysm clip applier circumvents one of the previously described problems, it is not capable of alleviating any contortion of the hand, wrist or arm of a surgeon.

U.S. Pat. No. 4,241,734 to Kandel et al issued on Dec. 30, 1980, discloses a shackle with a tubular member mounted on the shackle. A rod with a clip grip is inserted into the tubular member. The clip is pulled by the rod into the tubular member which opens the clip. The rod is axially forced back out the tubular member to permit the clip to close. While this device has small dimensions adjacent the end of the tubular member, thereby utilizing a small hole in the brain, it does not alleviate any contortion of the hand, wrist or arm of the surgeon.

None of these conventional type clip aneurysm appliers is movable in a multitude of directions without the physician or surgeon contorting his or her hand, wrist or arm. None of the conventional clip aneurysm appliers include a mechanism for loading, retaining and applying an aneurysm clip which is not in alignment with the longitudinal axis of the appliers. Moreover, the conventional aneurysm clip appliers are designed to lie flat in one's hand and therefore are difficult to rotate in one's hand due to the planar portion of the elongated handle means and are not comfortably balanced as contrasted with an object having a rod-type hand grip.

SUMMARY OF THE INVENTION

The present invention relates to a well balanced, aesthetically pleasing, comfortable feeling tool designed to apply aneurysm clips from a wide variety of angles. Unlike prior art devices, the handle portion of the present invention is an elongated cylinder flared at each end and having a stippled surface to prevent slipping. Furthermore, the device includes a single spring loaded trigger which is easily operated by one's index finger enabling a surgeon to spread and apply an aneurysm clip. The tool also includes a barrel portion designed to rotate 360° to provide a multitude of directions for applying the aneurysm clip. The Y-shaped clip retainer preferably includes two projections designed to snuggly fit within complementary recesses of an aneurysm clip so that the clip itself is capable of pivoting about the axis of the projections, thereby increasing the angles at which the clip can be applied.

Lastly, the device includes a locking pin designed to retain an aneurysm clip within the retaining means of the pliers until the surgeon or physician is ready for its use, thereby preventing a surgeon from being burdened with loading the pliers.

In the broadest sense, the present invention concerns an aneurysm clip pliers for applying an aneurysm clip to a blood vessel comprising: a hand grip portion; a barrel portion secured to said hand grip portion, said barrel portion having a Y-shaped grip for holding an aneurysm clip, said Y-shaped grip including two arms, each pivotable with respect to said barrel portion; means to bias each of said arms open; and a pusher bar means designed to reciprocate within said barrel portion, said pusher bar means having a tapered end capable of being positioned between said arms to cause said arms to pivot in a closed position.

The present invention will be more fully understood and described with reference to the following drawings and complete description.

BRIEF DESCRIPTION OF THE DRAWINGS

FIG. 1 is a side elevational view of a full scale aneurysm clip pliers of the present invention.

FIG. 2 is an enlarged fragmentary cross-sectional side view of the end of the aneurysm clip pliers containing the retaining means designed to retain and apply the aneurysm clip.

FIG. 3 is an elevational full scale cross-sectional side view of the aneurysm clip pliers.

FIG. 4 is an enlarged fragmentary cross-sectional side view of the barrel end including the clip retaining means illustrating a clip in the partially opened position.

DESCRIPTION OF THE PREFERRED EMBODIMENTS

Figure 5:
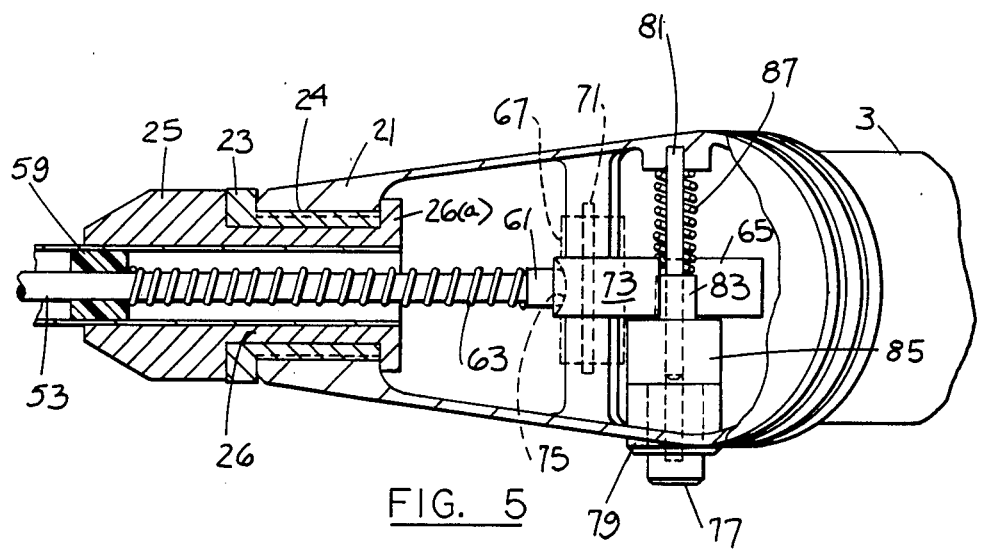
FIG. 5 is an enlarged fragmentary cross-sectional plan view illustrating the position of the locking means in the normal unlocked position.

An aneurysm is a ballooning of the blood vessel wall resulting from focal weakness and distention. The present invention is designed for use in surgical treatment of arterial and arteriovenus aneurysms of the brain. The present invention is particularly useful for treating aneurysms located deeply within the brain.

Typically, the location of the aneurysm is discovered by conventional techniques. A hole is then cut through the skull in an area convenient for treating the brain aneurysm. If the aneurysm is located deeply within the brain, a spatula-type implement is employed to "dig down" to the aneurysm. In other words, various portions of the brain are moved so as to expose the aneurysm deep within the brain. Using the aneurysm clip pliers of the present invention, an aneurysm clip is then clamped onto the blood vessel feeding the aneurysm to compress the blood vessel thereby reducing or eliminating the aneurysm so that the aneurysm will not rupture. Once the aneurysm clip is clamped on the blood vessel, the aneurysm clip pliers is removed from the hole in the cranium and the hole is surgically repaired or patched. The aneurysm clip is designed to be left within the brain permanently and does not interfere with the chemical composition of the brain or cause any complications.

The aneurysm clip pliers of the present invention may be made from any material capable of providing sufficient strength to apply an aneurysm clip and be cleanseable to remove any blood or tissue matter, and be capable of undergoing sterilization. Typically, plastics such as polyethylene or polypropylene are satisfactory because they can be economically manufactured, are light in weight and possess the traits of being both cleanseable and sterilizable. Also, metals which do not readily react with the blood or other bodily fluids, such as aluminum or stainless steel are satisfactory, since neither of these metals oxidize. Aluminum is sufficiently light weight and durable, making it the preferred material.

As illustrated in FIG. 1, the aneurysm clip pliers, as generally indicated by reference numeral 1, includes a hand grip end 3 and a barrel clip retaining end 5. The hand grip end 3 is a hollow elongated cylinder approximately 1 to 1¼ inches in diameter. While larger diameter cylinders could be employed, it has been found that the above range is suitable for most hand sizes.

The hand grip 3 terminates at each end with a flared portion 7 and 9. Between the pair of flared ends 7 and 9 on the tubular hand grip is stippling 11, shown in part in FIG. 1. The stippling 11 and the flared ends 7 and 9 prevent the surgeon or physician's hand from slipping from the hand grip 3. Because the hand grip 3 is cylindrical, it can easily be rotated in the surgeon's hand to achieve a better angle when applying the aneurysum clip.

Connected to the distal flared end 7 is a hollow circular end plug 13 which may optionally include stippling and/or grooves 15 to aid in gripping the tool. The circular end plug 13 is slightly larger in diameter than the stippled area 11 of the hand grip 3.

Likewise, attached to the flared end 9 is a hollow tubular portion 17 of the same diameter as the end plug 13 and having stippling and/or grooves 19 similar to the grooves 15.

The barrel end 5 of the aneurysm clip pliers includes at one end thereof a hollow tubular rod 21 secured to the cylindrical tube 17. The opposing end of the rod 21 is securely fastened to a stationary ring 23. Adjacent stationary ring 23 is a frustoconical link 25 which in turn is secured to hollow tubular wand 27. Rod 21, ring 23, link 25 and wand 27 are in alignment with one another and are preferably at an obtuse angle with respect to the hand grip portion 3. Both the link 25 and the wand 27 rotate with respect to the remainder of the aneurysm clip pliers 1, as illustrated by arrow A in FIG. 1. Rotation of wand 27 allows a wide variety of angles to be chosen by the surgeon when applying the clip.

Figure 6:
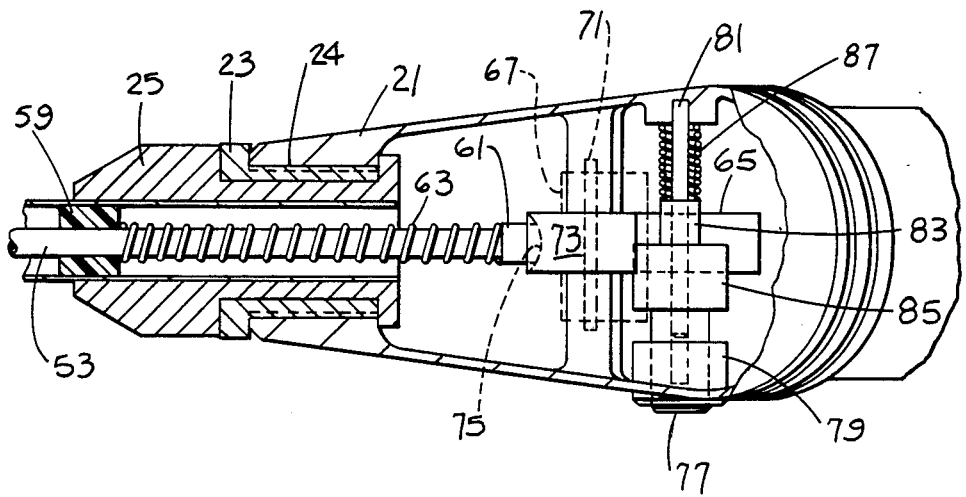
FIG. 6 is an enlarged fragmentary cross-sectional plan view illustrating the position of the locking means in the locked position.

The stationary ring 23 has a plurality of threads 24, securely fastening it to the rod 21. The link 25 includes a projecting tube 26 positioned concentrically inward of the ring 23, as illustrated in FIG. 5. The projecting tube 26 includes a flange 26a, adjacent the threaded end 24, having a larger diameter than the ring 23, as illustrated in FIGS. 5 and 6. In this manner, the ring 23 remains stationary with respect to the rod 21, while the link 25 and the wand 27 are capable of rotating through 360°.

The free end of the wand 27 provides a housing for a Y-shaped clip retaining grip 29. The Y-shaped retaining grip comprises two mirrow image arms 31 and 33. As clearly illustrated in FIG. 2, arms 31 and 33 preferably have a pair of opposed projections 35 and 37 positioned on the inside of each arm so that they face one another. These projections 35 and 37 engage corresponding dimples 39 and 41 in the aneurysm clip 43. This enables the aneurysm clip 43 to pivot about the axis of the projections 35 and 37 such that the clip 43 is capable of rotating upwardly with respect to the FIG. 1 drawing, downwardly with respect to the FIG. 1 drawing, and any position in between, thereby enabling the clip 43 to pivot about an arc slightly larger than 180°. In addition to the pliers being easily rotatable when held by the surgeon, and in addition to wand 27 being rotatable, this last feature, combined with the above features, gives a surgeon a wide latitude in applying a clip at a convenient, comfortable angle.

In general, the typical aneurysm clip is formed so that it is spring bias closed in the normal rest position. The clip is opened by squeezing the clip 43 so that the dimples 39 and 41 are moved toward one another.

Each arm 31 and 33 of the Y-shaped grip 29 is fastened to the wand 27 by means of a pair of hinge pins 45 and 47, as illustrated in FIG. 2. Each hinge pin projects entirely through the wand 27 and one of the arms. Accordingly, the Y-shaped grip 29 rotates with wand 27. Each arm 31 and 33 is capable of pivoting around the pins 45 and 47 to the extent permitted by the interior dimensions of the hollow wand 27. Each arm 31 and 33 includes a hole at its end opposite the projections 35,37, each hole being parallel with the axis of projections 35 and 37 and perpendicular to the hinge pins 45 and 47. In each hole is a resilient material 49 and 51 which is secured in the hole by means of compression or an adhesive. The resilient material 49 and 51 can be a medium or soft rubber or plastic, such as silicon rubber, butylstyrene rubber, or the like. The resilient material 49 and 51 functions to bias its respective arm 31 and 33 in the "open position". In the fully opened position, each arm 31 and 33 is positioned a slight distance from one another based upon the difference between the hinge pins 45 and 47.

Concentrically positioned within hollow wand 27 is a pusher bar 53 having a pointed or tapered end 55 whose tapered edge is spaced equidistant from each arm 31 and 33. The bar 53 is designed to longitudinally reciprocate within the hollow wand 27 toward or away from the Y-shaped grip 29. The pusher bar 53 is held in alignment for reciprocation by a guide bushing 57 which is securely fastened to the interior wall of the hollow wand 27. The bar 53 projects through the guide bushing 57. The guide bushing 57 is made of a material having a low co-efficient of friction such as polytetrafluoroethylene.

Illustrated in FIG. 3 is a second guide bushing 59 secured to the hollow wand 27 in much the same manner as guide bushing 57 and is made from the same type low co-efficient of friction material. The bar 53 additionally projects through the guide bushing 59. The end of the bar 53 opposite the tapered end includes a rounded head 61, as illustrated in FIGS. 3, 5 and 6. Head 61 has a diameter slightly larger than the diameter of the pusher bar 53. Concentrically positioned around the bar rod 53, between the guide bushing 59 and the head 61 is a coil spring 63.

Positioned at the juncture of the hand grip end 3 and the barrel end 5 is a trigger 65 having a lower curved portion 67 which projects out of a hole 69 in the hand grip portion 3. The trigger 65 is retained by and pivots around a hinge pin 71. The upper portion of trigger 65, as illustrated in FIG. 3, has a crown 73 having a dish shaped dimple 75, as illustrated in FIGS. 5 and 6. This dish shaped dimple 75 mates with the rounded head 61 of the pusher bar 53 so that when the trigger 65 is squeezed to retract within the hand grip end 3, the crown 73 thrusts the pusher bar 53 toward the Y-shaped grip 29. When the trigger 65 is released, the coil spring 63 naturally biases pusher rod 53 and crown 73 away from the Y-shaped grip 29.

A lock button 77 is parallel with hinge pin 71 and projects outwardly from the hollow circular portion 17, as illustrated in FIGS. 1, 5 and 6. The position of the button 77 indicates the pliers 1 illustrated in FIGS. 1–6 is right-handed because the button 77 is designed to be activated by the right thumb of the surgeon. Of course, the pliers 1 can easily be made left-handed by positioning button 77 in an opposite manner.

A low co-efficient of friction guide sleeve 79 permits the button 77 to reciprocate therethrough. The button 77 is fixedly secured to a shaft 81 at one end thereof, while the other end of shaft 81 is fixedly secured to the interior wall of hollow rod 21, as illustrated in FIGS. 5 and 6. Stationarily secured to shaft 81 are two cam surfaces 83 and 85. Cam surface 83 has a diameter smaller than cam surface 85 and is designed to contact trigger 65 when the pusher bar 53 is in its normal rest position, i.e., when spring 63 no longer exerts force on head 61. Small cam surface 83 also serves as a stop for one end of a coil spring 87 concentrically surrounding shaft 81. The other end of coil spring 87 is maintained by the interior of rod 21.

The large cam surface 85 engages trigger 65 in such a manner as to cause the trigger to pivot thrusting the crown 73 toward the Y-shaped grip 29, while the curved portion 67 is slightly recessed within hand grip end 3.

In operation, when it is desired to apply an aneurysm clip to a blood vessel of the brain, a surgical nurse or a surgeon merely positions an aneurysm clip 43 within the Y-shaped grip 29 between arms 31 and 33 so that the projections 35 and 37 are in alignment with the dimples 39 and 41 of the clip 43. The trigger is lightly squeezed so that it is slightly recessed within the hand grip 3 causing the crown 73 with the dish shaped dimple 75 to push upon head 61 causing pusher rod 53 to shift toward arms 31 and 33 until edge 55 is in contact with and slightly recessed between each arm 31 and 33, as illustrated in FIG. 3. The Y-shaped grip 29 now retains the aneurysm clip 43. Button 77 is now shoved inwardly, as illustrated in FIGS. 3 and 6, in order to retain the pusher bar 53 in a position to retain the aneurysm clip 43 without opening it.

At this point, the aneurysm clip pliers can be placed upon a surgical tray until the surgeon is ready to employ the aneurysm clip. The button 77 assures that the aneurysm clip 43 will be retained between the arms 31 and 33. In order for the button 77 to properly function, it will be necessary for spring 63 to provide a greater force against the crown 73 of trigger 65 (which in turn transfers that force to the large cam surface 85, as illustrated in FIG. 6) than the force of spring 87, which is now compressed, and is biasing the large cam surface 85 out of contact with trigger 65.

When the surgeon is ready to apply the aneurysm clip, he merely picks up the aneurysm clip pliers by hand grip end 3 and inserts the barrel end 5 into the brain after adjusting the angle of rotation of wand 27 and the angle of rotation of aneurysm clip 43 about the axis of the projections 35 and 37. The surgeon fully squeezes trigger 65 so that it recesses completely within the hand grip 3 causing the crown portion 73 to shift the pusher bar 53 well between the arms 31 and 33 causing the clip 43 to open, as illustrated in FIG. 4. When the trigger 65 is fully recessed within the hand grip 3, the aneurysm clip 43 opens much wider than illustrated in FIG. 4.

The degree to which the aneurysm clip is opened depends upon the angle of edge 55 of the pusher bar 53, the length of the arms 31 and 33 of the Y-shaped grip 29 and the travel distance of the crown 73 of trigger 65. By varying any one or more of these parameters, the aneurysm clips can be made to open or close as desired.

Once the aneurysm clip 43 is fully opened and the blood vessel is within the jaws of the clip, trigger 65 can be released, resulting in spring 63 forcing the crown 73 away from the Y-shaped grip 29 until the spring 63 no longer exerts any pressure against the head 61. In this condition, the clip 43 closes around the blood vessel and is no longer in contact with arms 31 and 33. Additionally, spring 87 now exerts a larger force against cam surface 83 (and corresponding cam surface 85) than the force exerted by spring 63, causing the button 77 to pop outwardly, as illustrated in FIG. 5. In this condition, the aneurysm clip plier is ready to retain and apply another aneurysm clip if it is so desired.

Modification of the present invention can be made without departing from the spirit of it.

What is claimed is:

1. An aneurysm clip pliers for applying an aneurysm clip to a blood vessel comprising: a hand grip portion; a barrel portion having a first end connected to said hand grip portion and a second end including a Y-shaped grip for holding an aneurysm clip, said Y-shaped grip including two arms, each of said arms being pivotally connected to said barrel portion about its own hinge pin; means connected to each of said arms to bias each of said arms open; and a pusher bar means inserted within said barrel portion, said pusher bar means having a tapered end capable of being positioned between said arms to cause said arms to pivot in a closed position.

2. Pliers for applying an aneurysm clip to a blood vessel, comprising:
   (a) a hand grip portion having a trigger;
   (b) a barrel portion removably connected at a first end to said hand grip portion, said barrel portion having a second end comprising a Y-shaped grip including:
      (i) a first arm, having a forward end and an aft end, pivotably connected to said barrel portion about a first hinge pin;
      (ii) a second arm, having a forward end and an aft end, pivotably connected to said barrel portion about a second hinge pin, whereby said forward ends of said arms cooperate to hold an aneurysm clip; and
      (iii) means connected to each of said arms and to said barrel portion to bias said arms in an open position to receive an aneurysm clip; and
   (c) pusher bar means, inserted in said barrel portion, coupled at a first rounded end with said trigger and at a second tapered end with said Y-shaped grip; whereby said trigger is actuated to force said pusher bar means between said aft ends of said arms to close said Y-shaped grip.

3. The pliers of claim 2 wherein said means to bias said arms in an open position comprises resilient material placed inside said barrel portion and secured to a hole in each arm between said hinge pins and said pusher bar means.

4. The pliers of claim 3 wherein said pusher bar means comprises a tubular bar having a tapered tip at its first end and a rounded head at its second end, said head being slightly larger in diameter than said bar.

5. The pliers of claim 4 wherein at least a portion of said barrel portion is rotatable through 360° with respect to said hand grip portion.

6. The pliers of claim 5 including locking means associated with said trigger for holding an aneurysm clip between said arms without the manual aid of the user.

7. Pliers for applying an aneurysm clip to a blood vessel, comprising:
   (a) a hand grip portion having a trigger;
   (b) a barrel portion removably connected at a first end to said hand grip portion, at least a portion of said barrel portion rotatable through 360° with respect to said hand grip portion, said barrel portion having a second end comprising a Y-shaped grip including:
      (i) a first arm, having a forward end and an aft end, pivotably connected to said barrel portion about a first hinge pin,
      (ii) a second arm, having a forward end and an aft end, pivotably connected to said barrel portion about a second hinge pin, whereby said forward ends of said arms cooperate to hold an aneurysm clip; and
      (iii) resilient means connected to a hole in each of said arms and to said barrel portion to bias said arms in an open position to receive an aneurysm clip;
   (c) pusher bar means, inserted in said barrel portion, coupled at a first rounded end with said trigger and at a second tapered end with said aft ends of said arms of said Y-shaped grip; and
   (d) locking means associated with said hand grip portion for holding an aneurysm clip between said arms without the manual aid of the user.

* * * * *